(12) United States Patent
Asamori

(10) Patent No.: US 7,201,806 B2
(45) Date of Patent: Apr. 10, 2007

(54) WASHING METHOD

(75) Inventor: Katsuhiko Asamori, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/175,331

(22) Filed: Jul. 7, 2005

(65) Prior Publication Data
US 2006/0011218 A1    Jan. 19, 2006

(30) Foreign Application Priority Data
Jul. 8, 2004    (JP)    ............... 2004-201894

(51) Int. Cl.
*B08B 3/04*    (2006.01)
(52) U.S. Cl. .................. 134/26; 134/2; 134/3; 134/28; 134/42; 424/661
(58) Field of Classification Search .................. 134/26, 134/2, 3, 42, 28; 424/661
See application file for complete search history.

(56) References Cited

U.S. PATENT DOCUMENTS

| | | | | |
|---|---|---|---|---|
| 3,717,580 A | * | 2/1973 | Echols et al. | 422/37 |
| 4,167,561 A | * | 9/1979 | Lamberti et al. | 424/665 |
| 4,908,215 A | * | 3/1990 | Perlman | 424/661 |
| 5,575,945 A | * | 11/1996 | Perlman | 252/176 |

FOREIGN PATENT DOCUMENTS

| | | |
|---|---|---|
| JP | 64-1152 A | 1/1989 |
| JP | 10-235335 A | 9/1998 |

* cited by examiner

*Primary Examiner*—Sharidan Carrillo
(74) *Attorney, Agent, or Firm*—Birch, Stewart, Kolasch & Birch, LLP

(57) ABSTRACT

The present invention includes disinfection washing of an object, with a washing solution 1 containing a chlorine-based disinfection detergent, and subsequent acid-washing of the object of washing, with a washing solution 2 adjusted to pH 4 or less by adding a reducing agent to the washing solution 1. This method is applicable as a method of washing artificial hemodialysis instruments used in hospitals etc.

16 Claims, No Drawings

WASHING METHOD

FIELD OF THE INVENTION

The present invention relates to a method of washing medical instruments, various industrial facilities etc. and particularly to a method of washing artificial hemodialysis instruments.

BACKGROUND OF THE INVENTION

A combination of washing with a chlorine-based disinfection detergent such as an aqueous solution of sodium hypochlorite and acid-washing with an aqueous acidic solution is generally carried out in washing medical instruments and facilities for producing medical preparations and foods. Pipes having an ultrafiltration membrane or a precision filtration membrane arranged therein for water treatment or the like, and these membranes, are washed by a combination of acid-washing with an aqueous acidic solution and alkali washing with an aqueous alkaline solution. Further, when medical instruments such as artificial hemodialysis instruments are disinfected and washed, sodium hypochlorite and acetic acid are known as the detergent used very frequently at present.

In particular, a chlorine-based disinfection detergent represented by sodium hypochlorite is used in a wide variety of applications such as washing of artificial hemodialysis instruments, etc. because of its strong sterilizing properties and its power to remove organic dirt such as protein and lipid.

Washing waste water using the chlorine-based disinfection detergent is desired to be disposed of after active chlorine is reduced to the minimum degree, from the viewpoint of its influence on the environment. With this background given, JP-A 64-11552 discloses a disinfection method that involves disinfecting an instrument as a subject of disinfection, with an aqueous solution of sodium hypochlorite and then adding a reducing agent to the aqueous solution to decompose sodium hypochlorite with the reducing agent. JP-A 10-235335 discloses that a reducing agent whose aqueous solution is alkaline is used as a treating solution to make a chlorine-based bleaching disinfectant harmless. On one hand, acid-washing using an organic acid such as acetic acid is carried out for the purpose of removing scale, but its waste water has a high BOD value, thus giving rise to concern about its influence on the environment, and may be hazardous because it can dissolve and destroy concrete buildings to cause a severe accident.

SUMMARY OF THE INVENTION

The present invention relates to a method of washing an object, including conducting step 1 and then step 2, step 1: disinfection washing of an object with a washing solution 1 containing a chlorine-based disinfection detergent, step 2: acid-washing of the object with a washing solution 2 adjusted to pH 4 or less by adding a reducing agent to the washing solution 1.

Further, the present invention relates to a detergent kit composed of the chlorine-based disinfection detergent and the reducing agent used in the washing method of the present invention described above.

DETAILED DESCRIPTION OF THE INVENTION

It is desired that washing of artificial hemodialysis instruments among various medical instruments and industrial facilities is excellent in scale removability, protein removability, and rust prevention in addition to disinfection properties, and while satisfying these properties, can achieve sufficient waste water treatment, but it is hardly said that JP-A 64-11552 and JP-A 10-235335 supra sufficiently meet such demand.

Accordingly, the present invention provides a washing method wherein the influence, on the environment, of washing waste water from a washing solution using a chlorine-based disinfection detergent such as hypochlorite and from an acidic washing solution using an organic acid such as acetic acid can be reduced while high detergency is maintained.

The present invention provides a washing method which exhibits high detergency on medical instruments such as artificial hemodialysis instruments etc. and various industrial facilities and can reduce the burden of waste water on the environment. In the present invention, an object of washing is disinfected and washed with a washing solution 1 containing a chlorine-based disinfection detergent, and then the object of washing is subjected to acid-washing with a washing solution 2 adjusted to pH 4 or less by adding a reducing agent to the washing solution 1. This method can be applied effectively as a method of washing artificial hemodialysis instruments used in hospitals etc.

The washing method of the present invention enables sufficient washing without using an organic acid such as acetic acid used in acid-washing of medical instruments such as artificial hemodialysis instruments etc. and various industrial facilities, and can solve the problem of discharge of active chlorine into the environment and the problem of waste water from the acid-washing solution.

<Washing Solution 1>

The washing solution 1 contains a chlorine-based disinfection detergent. The chlorine-based disinfection detergent is preferably an alkali metal hypochlorite such as sodium hypochlorite, potassium hypochlorite or the like, an alkaline earth metal hypochlorite such as calcium hypochlorite, a chlorinated alkali metal isocyanurate such as chlorinated sodium isocyanurate, chlorinated potassium isocyanurate or the like, or a chlorinated alkaline earth metal isocyanurate such as chlorinated calcium isocyanurate or the like. Among these, an alkali metal hypochlorite such as sodium hypochlorite, potassium hypochlorite or the like is preferable, and sodium hypochlorite is more preferable. Generally, sodium hypochlorite is produced by blowing a chlorine gas into an aqueous solution of sodium hydroxide, and is used in the form of an aqueous solution where sodium hydroxide is present for stabilization of the aqueous solution. Even if the washing solution 1 containing the remaining alkali component such as sodium hydroxide is used, the alkali component is not problematic in such a range that it does not influence the reduction in pH by the reducing agent in step 2, and thus the alkali component is usually present in the washing solution 1 to which the reducing agent is to be added in step 2.

In respect of the disinfection washing effect, the available chlorine concentration in the washing solution 1 is preferably 50 to 5000 ppm, more preferably 200 to 2500 ppm, and the chlorine-based disinfection detergent is compounded preferably so as to meet this concentration. The available chlorine concentration may be the above-mentioned concentration in any point of time from the start to end of step 1, but is preferably in the above range, at least at the start of step 1 (initial concentration).

In respect of protein removability, the washing solution 1 is used preferably at pH 7 or more, more preferably at pH 9 or more. The adjustment of pH can be carried out by adding a suitable alkali and regulating its content.

<Washing Solution 2>

The washing solution 2 is the one whose pH was adjusted to 4 or less, preferably 3 or less, by adding a reducing agent to the washing solution 1 used in step 1 above. By using the washing solution 2 in this pH range, the effect of acid-washing is obtained.

The reducing agent is at least one member selected from thiosulfate, bisulfite, hyposulfite and ascorbate. Among these, thiosulfate is more preferable. These salts are preferably salts of an alkali metal such as sodium, potassium or the like. The reducing agent added in step 2 is used in a ratio of preferably 20 to 200 mol %, more preferably 25 to 150 mol %, still more preferably 30 to 100 mol %, relative to available chlorine in the washing solution 1, from the viewpoint of easy reduction in the pH of the resulting washing solution 2 and achievement of an excellent effect by acid-washing. The amount is further more preferably 25 to 30 mol %.

For example, when the reducing agent is sodium thiosulfate, its addition to an aqueous solution of sodium hypochlorite brings about inactivation of chlorine according to the reaction in the following reaction equations (1) and (2). Because the alkali component (sodium hydroxide etc.) is present in the washing solution 1 as described above, and thus the reaction equation (1) proceeds. A very small amount of chlorine is present in equilibrium in the aqueous solution of sodium hypochlorite, but when the pH is decreased in the reaction equation (1), chlorine is increased and the reaction equation (2) proceeds. When the amount of sodium thiosulfate added is suitably regulated, the pH is reduced due to acid generated in the reaction equation (2), and thus the solution can be used in acid-washing. That is, chlorine inactivation and acid-washing can be simultaneously realized in the present invention.

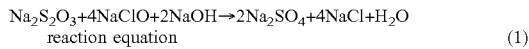

$$Na_2S_2O_3 + 4NaClO + 2NaOH \rightarrow 2Na_2SO_4 + 4NaCl + H_2O \quad \text{reaction equation} \quad (1)$$

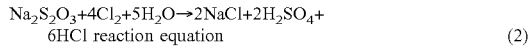

$$Na_2S_2O_3 + 4Cl_2 + 5H_2O \rightarrow 2NaCl + 2H_2SO_4 + 6HCl \quad \text{reaction equation} \quad (2)$$

<Other Components>

The washing solutions 1 and 2 can contain a surfactant, a chelating agent and/or a rust preventive. These components may be added previously to each of the washing solutions or may be added thereto during each step.

The surfactant includes anionic surfactants such as alkyl sulfate, polyoxyethylene alkyl ether sulfate, alkyl phenyl ether sulfate, alkyl diphenyl ether disulfonate, alkyl sulfonate, and polyoxyethylene alkyl ether acetate; nonionic surfactants such as polyoxyethylene alkyl ether, polyoxyethylene alkyl glyceryl ether, alkyl glyceryl ether, alkyl polyglycoside, polyoxyethylene/polyoxypropylene block copolymer, polyoxyethylene sorbitan fatty ester, tetra-fatty acid polyoxyethylene sorbit, and alkyl amine oxide; and amphoteric surfactants such as alkyl dimethyl aminoacetic acid betaine, alkyl-N-carboxymethyl-N-hydroxyethyl imidazolium betaine, fatty acid amide propyl betaine, and alkyl hydroxy sulfobetaine. The surfactant is preferably polyoxyethylene alkyl ether sulfate, alkyl phenyl ether sulfate, or alkyl diphenyl ether disulfonate. When the object of washing contains a filter absorbing a surfactant, a surfactant is preferably not used.

When a surfactant is added during each step, a higher detergent effect is obtained by adding the surfactant in a stage as early as possible in each step. The content of the surfactant is preferably 1 to 1000 ppm, more preferably 10 to 1000 ppm, still more preferably 50 to 500 ppm, in the washing solution 1 or 2.

The chelating agent includes condensed phosphates (pyrophosphate, tripolyphosphate, tetrapolyphosphate, hexapolyphosphate), polyacrylate, acrylate/maleate copolymers, organic phosphonates (aminotri(methylene phosphonate), 1-hydroxyethylidene-1,1-diphosphonate, ethylene diamine tetra(methylene phosphate), diethylene triamine penta(methylene phosphonate), phosphonobutane tricarboxylate) etc. The chelating agent is preferably a condensed phosphate or organic phosphonate. The content of the chelating agent in the washing solution 1 or 2 is preferably 1 to 1000 ppm, more preferably 10 to 500 ppm, still more preferably 20 to 200 ppm.

The rust preventives (some of which also function as a chelating agent) include silicates (orthosilicate, metasilicate, silicate No. 1 etc.), phosphate, nitrate, the organic phosphonate descried above, oxalate, borate etc. The rust preventive is preferably a silicate or the organic phosphonate described above. The content of the rust preventive in the washing solution 1 or 2 is preferably 0.001 to 200 ppm, more preferably 0.01 to 50 ppm, still more preferably 0.1 to 20 ppm.

<Washing Method>

In the present invention, after the disinfection washing (step 1) of an object of washing, with a washing solution 1 containing a chlorine-based disinfection detergent is conducted, the object of washing is subjected to acid-washing (step 2) with a washing solution 2 adjusted to pH 4 or less by adding a reducing agent to the washing solution 1. In both steps, the temperature of the washing solution can be 15 to 95° C. In particular, the temperature in step 1 is preferably 15 to 60° C., and the temperature in step 2 is preferably 30 to 60° C. It is important that the washing solution and the object of washing are contacted sufficiently with each other, and besides an immersion method, a method of regulating a flow rate during fluid passage or a method of regulating retention time after fluid passage can be utilized in the case of a washing line etc. When an object of washing is in a close system containing a fluid-sending line etc., a method of washing it at a suitable flow rate (for example 0.1 to 50 L/min.) under circulation is preferable. In addition, air bubbling and supersonic waves can also be simultaneously utilized.

In the present invention, it is preferable that the following step 3 is further conducted after step 2.

Step 3: Adjustment in the range of pH 5 to 9 by adding a reducing agent and/or an alkali to the washing solution 2 after step 2 is finished.

In the adjustment of pH in step 3, the reducing agent described in step 2 and an alkali can be used, and when the reducing agent is used, it is preferable from the viewpoint of easy pH adjustment and the COD value of waste water that the reducing agent is used in a ratio of 20 to 200 mol %, more preferably 25 to 150 mol %, still more preferably 30 to 100 mol %, relative to available chlorine in the washing solution 1. The ratio is also more preferably 30 to 45 mol %.

When the alkali is used in step 3, it is preferable from the viewpoint of easy pH adjustment that the alkali is used in a ratio of 10 to 100 mol %, more preferably 12 to 75 mol %, still more preferably 15 to 50 mol %, relative to available chlorine in the washing solution 1.

The washing solution 2 whose pH is adjusted in the range of 5 to 9 in step 3 is preferable because the solution can be disposed of as it is. Accordingly, the present invention may also include disposing of the washing solution whose pH is adjusted in step 3.

The alkali is for example at least one member selected from alkali metal hydroxides such as sodium hydroxide, potassium hydroxide etc. and alkali metal carbonates such as sodium carbonate, potassium carbonate etc. These alkalis are effective for adjustment of pH in the vicinity of the neutral range of pH 5 to 9 in step 3, and the amount of the alkali added may be regulated depending on the available chlorine concentration in the washing solution 1 and the amount of the reducing agent added. In step 3, the reducing agent or alkali may be added, or both the reducing agent and alkali may be added.

In carrying out the present invention, the reducing agent in step 2 and the reducing agent and/or alkali in step 3 are fed respectively as an aqueous solution containing these components from a supply tank to each washing solution. In step 3, chlorine in the washing solution 2 has previously been inactivated, and even a small amount of alkali component can easily increase the pH, and thus an aqueous solution containing the alkali component at a relatively low concentration can be used. On one hand, the presence of a small amount of alkali component is allowable in step 2 as well and thus it is preferable that the same aqueous solution containing the reducing agent and alkali can be used in steps 2 and 3 to simplify facilities. For example, when the reducing agent is sodium thiosulfate and the alkali is sodium hydroxide, the reducing agent/alkali ratio by weight is preferably 10/1 to 5/1. As a matter of course, the alkali is essentially not necessary from the viewpoint of adjustment of pH in step 2, and thus a means may be arranged respectively for supplying the reducing agent in step 2, the reducing agent in step 3, and the alkali in step 3, and can be used supply the respective components separately. The temperature in step 3 is preferably 15 to 95° C., more preferably 15 to 60° C.

A detergent kit for the washing method of the present invention can be constituted from the chlorine-based disinfection detergent described above and the reducing agent capable of adjustment to pH 4 or less by addition thereof to the washing solution 1.

EXAMPLES

Example 1

A hemodialysis apparatus DBG-01, single patient unit, manufactured by Nikkiso, was used as an object of washing, to evaluate washing properties. A part of a line of this instrument was replaced by a silicon tube contaminated under the conditions described below, and when the steps 1, 2 and 3 were finished, the silicon tube was removed to evaluate the contaminated state of the inside of the tube in the following manner.

(1) Conditions for Contaminating the Silicon Tube

A silicon tube of about 40-cm was charged with a standard hemodialysis solution (Kindaly Solution AF-1, Fuso Yakuhin Kougyou) and left sidewise for 1 week. After precipitation of calcium carbonate was confirmed, a supernatant was disposed. 0.5 mL of horse serum was then dropped onto the inner surface of the silicon tube, and the horse serum was fixed onto the silicone tube by thermal deterioration at 50° C. for 24 hours on the tube placed sidewise. The amount of calcium carbonate adhering to the contaminated silicon tube obtained in this procedure was 6.0 to 7.0 mg/m per meter of the tube.

(2) Evaluation Method (2-1) Method of Evaluating Protein Dirt

After the silicon tube was washed, the tube was removed and an about 5-cm area of the tube, containing a part stained with blood (horse serum), was divided vertically, and the state of adhering protein was evaluated with naked eyes by an amide black staining method.

(2-2) Method of Evaluating the Amount of Adhering Calcium Carbonate

The remainder of the silicon tube, about 30 cm, was filled therein with 0.1 N hydrochloric acid solution to elute calcium carbonate therefrom, and the Ca concentration of the eluate was measured to determine the amount of adhering calcium carbonate. The amount of adhering calcium carbonate was expressed in unit "mg/m" per meter of the silicon tube.

(3) Washing and Evaluation Results

The measurement of the pH and available chlorine concentration of the washing solution in each step was carried out by arranging a sampling port just before the silicon tube for dirt evaluation and then sampling the circulating washing solution through an injection syringe.

A chlorine-based detergent tank was charged with a primary dilution prepared by 1.4-fold dilution, with water, of an aqueous chlorine-based detergent stock solution containing 7.2 wt % (as available chlorine) sodium hypochlorite, 0.02 wt % sodium metasilicate and 1.4 wt % sodium tripolyphosphate. The primary chlorine-based detergent dilution was fed to a washing line of an object filled with water purified by reverse osmosis (referred to hereinafter as RO water) to prepare a washing solution 1 at an available chlorine concentration of 1010 ppm. The reduction in the weight of the primary dilution in the chlorine-based detergent tank was 10.57 g. The pH of this washing solution 1 was 10.6. A washing line of an object was washed at 36° C. with the washing solution 1 circulated for 40 minutes at a flow rate of 0.5 L/min. (step 1).

Thereafter, 1.94 g aqueous reducing agent stock solution containing 20.0 wt % sodium thiosulfate and 3.2 wt % NaOH (sodium thiosulfate was 32.1 mol % relative to available chlorine in the washing solution 1) was introduced from a reducing agent supply tank to the line to be washed. It was confirmed that the pH of the washing solution after 50 minutes was reduced to 2.75, and the available chlorine concentration became less than the detectable lower limit of 0.05 ppm. This acidic solution was used as the washing solution 2 and circulated at a flow rate of 0.5 L/min. for 30 minutes to conduct acid-washing at 36° C. (step 2) for the purpose of removing scale components such as calcium carbonate.

Thereafter, 1.90 g of the same aqueous reducing agent stock solution was introduced into the line to be washed, and was circulated under the same conditions as described above. The pH of the washing solution after 5 minutes was 6.12, and the available chlorine concentration was less than the detectable lower limit of 0.05 ppm. The pH of the washing solution after 2 hours was 6.05 (step 3).

After step 3, the silicon tube for dirt evaluation was removed and measured for the amounts of adhering protein and calcium carbonate by the method described above, and as a result, the adhesion of protein was not recognized, and the amount of adhering calcium carbonate was 0.01 mg/m, and almost all calcium carbonate having adhered before washing was removed.

Example 2

The evaluation was conducted in the same manner as in Example 1 by the following method. A chlorine-based detergent tank was charged with a primary dilution prepared by 1.4-fold dilution, with water, of an aqueous chlorine-based detergent stock solution containing 7.0 wt % (as available chlorine) sodium hypochlorite and 0.02 wt % sodium metasilicate. 10.68 g of the primary chlorine-based detergent dilution was fed to a washing line of an object filled with RO water to prepare a washing solution 1 at an available chlorine concentration of 992 ppm. The pH of this washing solution was 10.6, and the washing line of an object was washed under heating at 60° C. with the washing solution circulated for 40 minutes at a flow rate of 0.5 L/min. (step 1).

Thereafter, 1.94 g aqueous reducing agent stock solution containing 20.0 wt % sodium thiosulfate and 3.2 wt % NaOH (sodium thiosulfate was 32.6 mol % relative to available chlorine in the washing solution 1) was introduced from a reducing agent supply tank to the line to be washed. It was confirmed that the pH of the washing solution after 5 minutes was reduced to 2.75, and the available chlorine concentration became less than the detectable lower limit of 0.05 ppm. This acidic solution was used as the washing solution 2 and circulated at a flow rate of 0.5 L/min. for 30 minutes to conduct acid-washing at 60° C. (step 2) for the purpose of removing scale components such as calcium carbonate.

Thereafter, 1.90 g of the same aqueous reducing agent stock solution was introduced into the line to be washed, and was circulated under the same conditions as described above. The pH of the washing solution after 5 minutes was 6.12, and the available chlorine concentration was less than the detectable lower limit of 0.05 ppm. The pH of the washing solution after 2 hours was 6.15 (step 3).

After step 3, the silicon tube for dirt evaluation was removed and measured for the amounts of adhering protein and calcium carbonate by the method described above, and as a result, the adhesion of protein was not recognized, and the amount of adhering calcium carbonate was 0.01 mg/m, and almost all calcium carbonate having adhered before washing was removed.

Example 3

A chlorine-based detergent tank was charged with a primary dilution prepared by 1.4-fold dilution, with water, of the same aqueous chlorine-based detergent stock solution as in Example 1. The primary chlorine-based detergent dilution was fed to a washing line of an object filled with by RO water to prepare a washing solution 1 at an available chlorine concentration of 480 ppm. The reduction in the weight of the primary dilution in the chlorine-based detergent tank was 5.02 g. The pH of this washing solution was 10.4. The washing line of an object was washed at 25° C. with the washing solution 1 circulated for 40 minutes at a flow rate of 0.5 L/min. (step 1).

Thereafter, 1.61 g aqueous reducing agent stock solution containing 10.0 wt % sodium thiosulfate, 1.5 wt % NaOH and 3.0 wt % sodium bisulfite (sodium thiosulfate was 28.0 mol % relative to available chlorine in the washing solution 1) was introduced from a reducing agent supply tank to the line to be washed. It was confirmed that the pH of the washing solution after 5 minutes was reduced to 3.02, and the available chlorine concentration became less than the detectable lower limit of 0.05 ppm. This acidic solution was used as the washing solution 2 and circulated at a flow rate of 0.5 L/min. for 30 minutes to conduct acid-washing at 25° C. (step 2) for the purpose of removing scale components such as calcium carbonate.

Thereafter, 1.60 g of the same aqueous reducing agent stock solution was introduced into the line to be washed, and was circulated under the same conditions as described above. The pH of the washing solution after 15 minutes was 5.95, and the available chlorine concentration was less than the detectable lower limit of 0.05 ppm (step 3).

After step 3, the silicon tube for dirt evaluation was removed and measured for the amounts of adhering protein and calcium carbonate by the method described above, and as a result, the adhesion of protein was not recognized, and the amount of adhering calcium carbonate was 0.01 mg/m, and almost all calcium carbonate having adhered before washing was removed.

Example 4

The steps 1 and 2 were conducted in the same manner as in Example 1. After step 2, the silicon tube for dirt evaluation was removed and then measured for the amounts of adhering protein and calcium carbonate by the method described above, and as a result, the adhesion of protein was not recognized, and the amount of adhering calcium carbonate was 0.01 mg/m, and almost all calcium carbonate having adhered before washing was removed.

Example 5

The steps 1 and 2 were conducted in the same manner as in Example 2. After step 2, the silicon tube for dirt evaluation was removed and then measured for the amounts of adhering protein and calcium carbonate by the method described above, and as a result, the adhesion of protein was not recognized, and the amount of adhering calcium carbonate was 0.01 mg/m, and almost all calcium carbonate having adhered before washing was removed.

Example 6

A chlorine-based detergent tank was charged with a primary dilution prepared by 1.4-fold dilution, with water, of the same aqueous chlorine-based detergent stock solution as in Example 1. The primary chlorine-based detergent dilution was fed to a washing line of an object filled with RO water to prepare a washing solution 1 at an available chlorine concentration of 1030 ppm. The reduction in the weight of the primary dilution in the chlorine-based detergent tank was 10.80 g. The pH of this washing solution was 10.6. The washing line of an object was washed at 40° C. with the washing solution 1 circulated for 40 minutes at a flow rate of 0.5 L/min. (step 1).

Thereafter, 11.07 g aqueous reducing agent stock solution containing 2.9 wt % sodium thiosulfate and 0.4 wt % NaOH (sodium thiosulfate was 26.0 mol % relative to available chlorine in the washing solution 1) was introduced from a reducing agent supply tank to the line to be washed. It was confirmed that the pH of the washing solution after 25 minutes was reduced to 2.78, and the available chlorine concentration became less than the detectable lower limit of 0.05 ppm. This acidic solution was used as the washing solution 2 and circulated at a flow rate of 0.5 L/min. for 30 minutes to conduct acid-washing at 40° C. (step 2) for the purpose of removing scale components such as calcium carbonate.

Thereafter, 8.53 g of the same aqueous reducing agent stock solution was introduced into the line to be washed, and was circulated under the same conditions as described above. The pH of the washing solution after 15 minutes was 6.52, and the available chlorine concentration was less than the detectable lower limit of 0.05 ppm (step 3).

Example 7

A chlorine-based detergent tank was charged with a primary dilution prepared by 2.0-fold dilution, with water, of the same aqueous chlorine-based detergent stock solution as in Example 1. The primary chlorine-based detergent dilution was fed to a washing line of an object filled with RO water to prepare a washing solution 1 at an available chlorine concentration of 880 ppm. The reduction in the weight of the primary dilution in the chlorine-based detergent tank was 13.18 g. The pH of this washing solution was 10.2. The washing line of an object was washed at 40° C. with the washing solution 1 circulated for 40 minutes at a flow rate of 0.5 L/min. (step 1).

Thereafter, 33.0 g aqueous reducing agent stock solution containing 0.8 wt % sodium thiosulfate and 0.11 wt % NaOH (sodium thiosulfate was 25.0 mol % relative to available chlorine in the washing solution 1) was introduced from a reducing agent supply tank to the line to be washed. It was confirmed that the pH of the washing solution after 25 minutes was reduced to 2.95, and the available chlorine concentration became less than the detectable lower limit of 0.05 ppm. This acidic solution was used as the washing solution 2 and circulated at a flow rate of 0.5 L/min. for 30 minutes to conduct acid-washing at 40° C. (step 2) for the purpose of removing scale components such as calcium carbonate.

Thereafter, 26.0 g of the same aqueous reducing agent stock solution was introduced into the line to be washed, and was circulated under the same conditions as described above. The pH of the washing solution after 15 minutes was 5.80, and the available chlorine concentration was less than the detectable lower limit of 0.05 ppm (step 3).

Test Example 1

The amount (mol %) of the reducing agent used in step 2, added to an aqueous solution containing sodium hypochlorite at an available chlorine concentration of 1000 ppm, the pH of the aqueous solution after addition of the reducing agent, and the available chlorine concentration were measured. The results are shown in Table 1.

TABLE 1

| Reducing agent | | Aqueous solution of sodium hypochlorite | |
|---|---|---|---|
| Type | Addition amount (mol %[1]) | pH[2] | Available chlorine concentration[3] |
| Sodium thiosulfate | 20.8 | 6.44 | 170 ppm |
| | 22.0 | 3.95 | 118 ppm |
| | 22.9 | 3.15 | 84 ppm |
| | 25.2 | 2.81 | less than 0.05 ppm |
| | 28.0 | 2.73 | less than 0.05 ppm |
| | 32.0 | 2.82 | less than 0.05 ppm |
| | 34.0 | 2.90 | less than 0.05 ppm |
| | 38.0 | 2.91 | less than 0.05 ppm |
| | 42.0 | 2.92 | less than 0.05 ppm |
| | 50.0 | 2.96 | less than 0.05 ppm |
| | 58.0 | 3.06 | less than 0.05 ppm |
| | 62.0 | 6.01 | less than 0.05 ppm |
| Sodium bisulfite | 24.0 | 7.82 | 660 ppm |
| | 49.1 | 6.53 | 500 ppm |
| | 72.6 | 2.40 | 275 ppm |
| | 106.8 | 2.04 | less than 0.05 ppm |
| | 155.0 | 2.12 | less than 0.05 ppm |
| Sodium hyposulfite | 25.6 | 7.23 | 230 ppm |
| | 49.5 | 2.33 | less than 0.05 ppm |
| | 76.4 | 2.30 | less than 0.05 ppm |
| | 97.8 | 2.28 | less than 0.05 ppm |
| | 124.7 | 2.30 | less than 0.05 ppm |
| | 167.0 | 2.38 | less than 0.05 ppm |
| Ascorbic acid | 25.3 | 7.06 | 746 ppm |
| | 51.0 | 3.43 | 490 ppm |
| | 75.8 | 3.23 | 240 ppm |
| | 94.4 | 3.13 | 52 ppm |
| | 138.4 | 3.22 | less than 0.05 ppm |

[1]Mol % relative to available chlorine in the aqueous solution
[2]pH after addition of the reducing agent
[3]Available chlorine concentration after addition of the reducing agent As can be seen from the reaction equations (1) and (2) above, sodium thiosulfate can inactivate chlorine by addition thereof in an amount of 25 mol % relative to available chlorine. In the results in Table 1, it can be confirmed that chlorine is not detected upon addition of sodium thiosulfate in an amount of 25 mol % or more. Chlorine can be inactivated by adding sodium bisulfite in an amount of 100 mol %, sodium hyposulfite 50 mol %, or ascorbic acid 100 mol %. For obtaining an acidic solution of pH 4 or less, it is not always necessary to add the reducing agent until the whole chlorine is inactivated. When the reducing agent in step 2 is sodium thiosulfate, it is added in an amount of 20 to 35 mol % relative to available chlorine. When the reducing agent in step 2 is sodium bisulfite, sodium hyposulfite or ascorbic acid, their amounts are preferably 90 to 130 mol %, 40 to 60 mol %, and 90 to 130 mol %, respectively. Out of the aqueous solutions described above, a solution of pH 4 or less can be used as the washing solution 2 in the present invention, but after step 2, the reducing agent is added preferably at a final concentration higher than the concentration of the reducing agent (mol %) inactivating the whole chlorine (step 3). Even when the reducing agent is added in excess, it disappears easily by airing in a septic tank or the like, thus exerting no serious adverse influence on the environment.

Test Example 2

A change in pH with time was measured in the case where to an aqueous solution containing sodium hypochlorite at an available chlorine concentration of 5020 ppm (aqueous solution 1) were added 20 mol % (relative to available chlorine) reducing agent sodium thiosulfate and 19.7 mol % (relative to available chlorine) alkali NaOH (aqueous solution 2), and to the aqueous solution 2 were added the same amounts of sodium thiosulfate and NaOH (aqueous solution 3). The results are shown in Table 2.

TABLE 2

| aqueous solutions | | Available chlorine concentration | pH |
|---|---|---|---|
| Aqueous solution 1 (Aqueous solution of sodium hypochlorite) | 10 minutes after preparation | 5020 ppm | 11.55 |
| | 40 minutes after preparation | 5000 ppm | 11.55 |
| Aqueous solution 2 (Aqueous solution 1 + reducing agent + NaOH) | 10 minutes after addition of the reducing agent | 1000 ppm | 3.95 |
| | 30 minutes after addition of the reducing agent | 996 ppm | 3.73 |
| Aqueous solution 3 (aqueous solution 2 + reducing agent + NaOH) | 10 minutes after addition of the reducing agent | less than 0.05 ppm | 6.82 |
| | 30 minutes after addition of the reducing agent | less than 0.05 ppm | 6.90 |

When the same evaluation as in Example 1 was conducted using the aqueous solutions 1 and 2 in Table 2 above, calcium carbonate and protein dirt could be removed almost completely.

The invention claimed is:

1. A method of washing a medical instrument or industrial facility, comprising the steps of:
   Step 1: disinfection washing said medical instrument or industrial facility with a washing solution 1 comprising a chlorine-based disinfection detergent having a pH of 7 or more, and
   Step 2: admixing said washing solution 1 with a first reducing agent subsequent to said washing in step 1 to adjust the pH of said solution to a pH of 4 or less to form a washing solution 2; and
   acid-washing said medical instrument or industrial facility with said washing solution 2.

2. The washing method according to claim 1, which further comprises conducting, after the acid washing in step 2.
   Step 3: adjusting said pH of washing solution 2 to a pH in the range of 5 to 9 by adding a second reducing agent and/or an alkali to the washing solution 2 after step 2 is finished.

3. The washing method according to claim 1 or 2, wherein the chlorine-based disinfection detergent is at least one member selected from the group consisting of hypochlorite and chlorinated isocyanurate.

4. The washing method according to claim 1 or 2, wherein the amount of the first reducing agent added in step 2 is 20 to 200 mol % relative to available chlorine in the washing solution 1.

5. The washing method according to claim 1 or 2, wherein said medical instrument to be washed is an artificial hemodialysis instrument.

6. The washing method according to claim 1 or 2, wherein at least one of the washing solution 1 and the washing solution 2 comprises a rust preventive and/or a chelating agent.

7. The washing method according to claim 2, wherein the amount of the second reducing agent added in step 3 is 20 to 200 mol % relative to available chlorine in the washing solution 1.

8. The washing method according to claim 2, wherein the amount of the alkali added in step 3 is 10 to 100 mol % relative to available chlorine in the washing solution 1.

9. A method of washing a medical instrument or industrial facility, comprising the steps of:
   Step 1: disinfection washing said medical instrument or industrial facility with a washing solution 1 comprising a chlorine-based disinfection detergent having a pH of 7 or more, and
   Step 2: admixing said washing solution 1 with a first reducing agent subsequent to said washing in step 1 to adjust the pH of said solution to a pH of 4 or less to form a washing solution 2; and
   acid-washing said medical instrument or industrial facility with said washing solution 2 wherein the first reducing agent is at least one member selected from the group consisting of thiosulfate, bisulfite, hyposulfite and ascorbate.

10. The washing method according to claim 9, which further comprises conducting, after the acid washing in step 2,
    Step 3: adjusting said pH of washing solution 2 to a pH in the range of 5 to 9 by adding a second reducing agent and/or an alkali to the washing solution 2 after step 2 is finished.

11. The washing method according to claim 9 or 10, wherein the chlorine-based disinfection detergent is at least one member selected from the group consisting of hypochlorite and chlorinated isocyanurate.

12. The washing method according to claim 9 or 10, wherein the amount of the first reducing agent added in step 2 is 20 to 200 mol % relative to available chlorine in the washing solution 1.

13. The washing method according to claim 9 or 10, wherein said medical instrument to be washed is an artificial hemodialysis instrument.

14. The washing method according to claim 9 or 10, wherein at least one of the washing solution 1 and the washing solution 2 comprises a rust preventive and/or a chelating agent.

15. The washing method according to claim 10, wherein the amount of the second reducing agent added in step 3 is 20 to 200 mol % relative to available chlorine in the washing solution 1.

16. The washing method according to claim 10, wherein the amount of the alkali added in step 3 is 10 to 100 mol % relative to available chlorine in the washing solution 1.

* * * * *